(12) United States Patent
Valdastri et al.

(10) Patent No.: US 10,722,171 B2
(45) Date of Patent: Jul. 28, 2020

(54) DEVICE FOR MEASURING A PLURALITY OF PARAMETERS IN PATIENT SUBJECT TO A TREATMENT WITH RADIOPHARMACEUTICALS

(71) Applicant: WINMEDICAL S.R.L., Pisa (IT)

(72) Inventors: Pietro Valdastri, Leghorn (IT); Ferdinando De Negri, Pisa (IT)

(73) Assignee: WINMEDICAL S.R.L., Cascina (IT)

( * ) Notice: Subject to any disclaimer, the term of this patent is extended or adjusted under 35 U.S.C. 154(b) by 1016 days.

(21) Appl. No.: 15/116,330

(22) PCT Filed: Feb. 16, 2015

(86) PCT No.: PCT/IB2015/051128
§ 371 (c)(1),
(2) Date: Aug. 3, 2016

(87) PCT Pub. No.: WO2015/121843
PCT Pub. Date: Aug. 20, 2015

(65) Prior Publication Data
US 2017/0007177 A1 Jan. 12, 2017

(30) Foreign Application Priority Data
Feb. 17, 2014 (IT) ................................ PI2014A0013

(51) Int. Cl.
*A61B 5/00* (2006.01)
*G06F 19/00* (2018.01)
(Continued)

(52) U.S. Cl.
CPC ............ *A61B 5/4848* (2013.01); *A61B 5/002* (2013.01); *A61B 5/02055* (2013.01); *A61B 5/48* (2013.01);
(Continued)

(58) Field of Classification Search
CPC .................................................... A61B 5/4848
See application file for complete search history.

(56) References Cited

U.S. PATENT DOCUMENTS

| 5,007,427 A | 4/1991 | Suzuki et al. |
| 5,647,363 A | 7/1997 | Rabito et al. |

(Continued)

FOREIGN PATENT DOCUMENTS

WO    2009/127954 A2    10/2009

OTHER PUBLICATIONS

International Search Report dated Jul. 17, 2015 for Application No. PCT/IB2015/051128.
(Continued)

*Primary Examiner* — Rochelle D Turchen
(74) *Attorney, Agent, or Firm* — Ladas & Parry LLP; Malcolm J. MacDonald

(57) ABSTRACT

A device for measuring a plurality of parameters of a patient subject to a treatment with radiopharmaceuticals includes a main body constrained to the patient's body in such a way that the measurement device is of wearable type. The device includes a plurality of measurement modules, for example a first module and a second module, each of which is equipped with a respective sensor, configured to measure a predetermined parameter of the patient. The device is also equipped with a microprocessor configured to process a plurality of data measured by the plurality of sensors, obtaining a plurality of processed data. Furthermore, a transmission means is provided of wireless type arranged to send via wireless communication the data processed by the microprocessor to a remote control unit.

12 Claims, 14 Drawing Sheets

(51) Int. Cl.
*G16H 40/63* (2018.01)
*G16H 50/50* (2018.01)
*A61B 5/0205* (2006.01)
*A61B 6/00* (2006.01)
*A61N 5/10* (2006.01)
*A61B 5/021* (2006.01)
*A61B 5/024* (2006.01)
*A61B 5/0402* (2006.01)
*A61B 5/08* (2006.01)
*A61B 5/11* (2006.01)
*A61B 5/145* (2006.01)

(52) U.S. Cl.
CPC .......... *A61B 5/6801* (2013.01); *A61B 5/6823* (2013.01); *A61B 5/6824* (2013.01); *A61B 5/7203* (2013.01); *A61B 6/42* (2013.01); *A61B 6/463* (2013.01); *A61N 5/1071* (2013.01); *A61N 5/1075* (2013.01); *G06F 19/3481* (2013.01); *G16H 40/63* (2018.01); *G16H 50/50* (2018.01); *A61B 5/021* (2013.01); *A61B 5/02438* (2013.01); *A61B 5/0402* (2013.01); *A61B 5/0816* (2013.01); *A61B 5/11* (2013.01); *A61B 5/14542* (2013.01); *A61B 2560/0456* (2013.01); *A61B 2562/06* (2013.01); *A61B 2562/18* (2013.01); *A61N 5/1001* (2013.01); *A61N 2005/1021* (2013.01)

(56) References Cited

U.S. PATENT DOCUMENTS

| | | |
|---|---|---|
| 2005/0287065 A1 | 12/2005 | Suddarth et al. |
| 2008/0146892 A1 | 6/2008 | LeBoeuf et al. |
| 2011/0137164 A1* | 6/2011 | Wise, III ............. G06F 19/3481 600/436 |
| 2015/0138547 A1* | 5/2015 | Burchard ............... G02B 5/008 356/326 |

OTHER PUBLICATIONS

Zuckier, L.S., et al., "Remotely Pollable Geiger-Müller Detector for Continuous Monitoring of Iodine-131 Therapy Patients", The Journal of Nuclear Medicine, vol. 39, No. 9, Sep. 1998, pp. 1558-1562.

Lee, J. H., et al., "Estimation of the Release Time from Isolation for Patients with Differentiated Thyroid Cancer Treated with High-dose I-131", Nucl Med. Mol. Imaging, Oct. 2010, vol. 44, pp. 241-245.

* cited by examiner

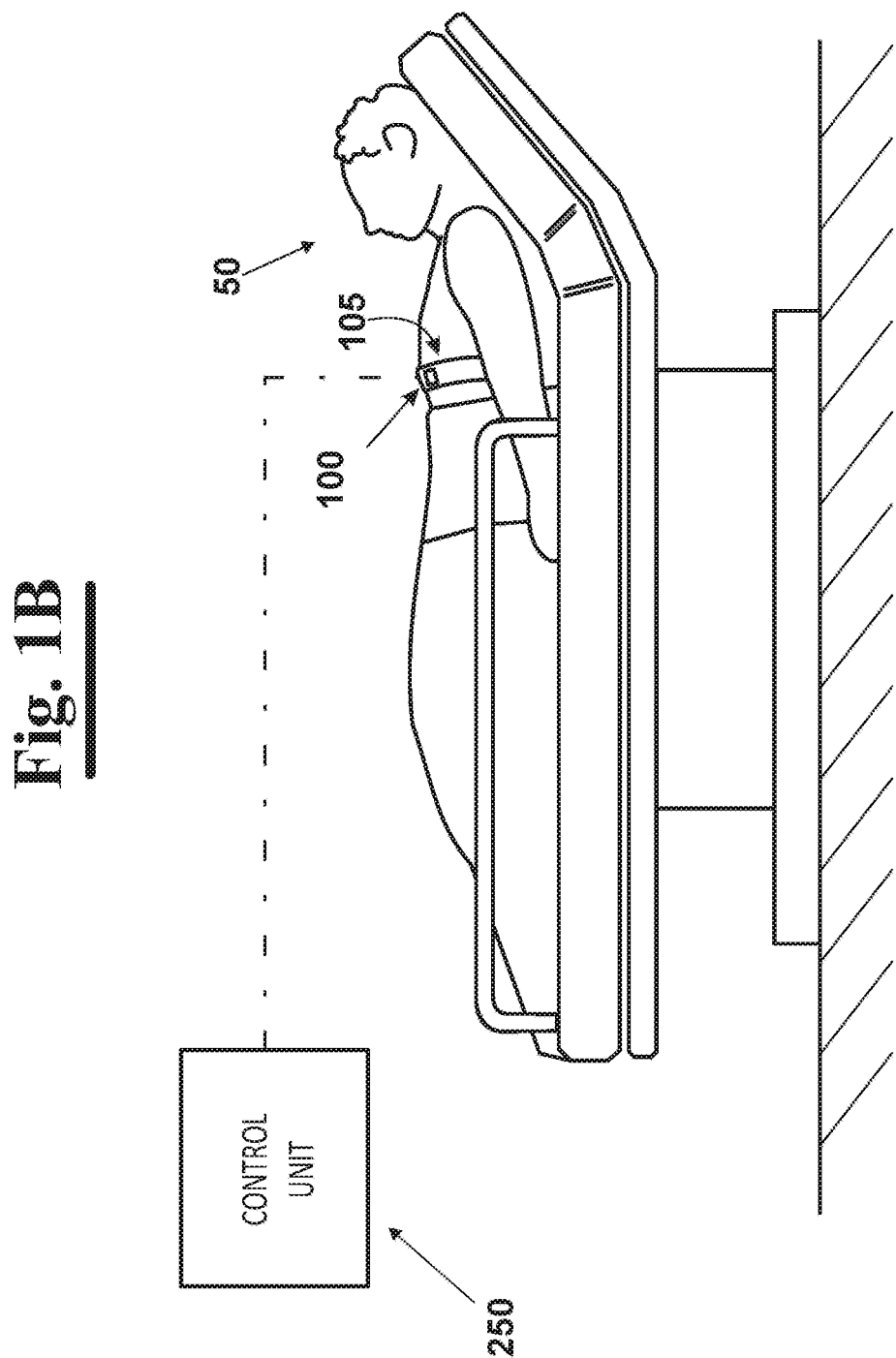

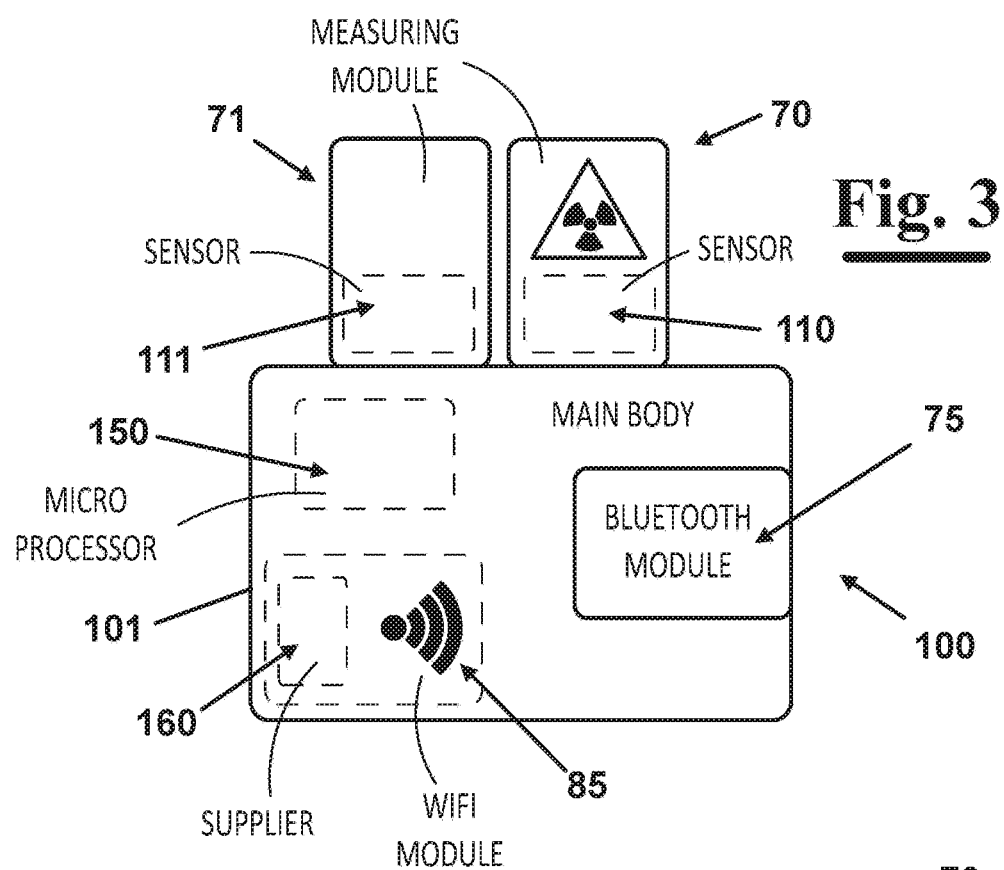
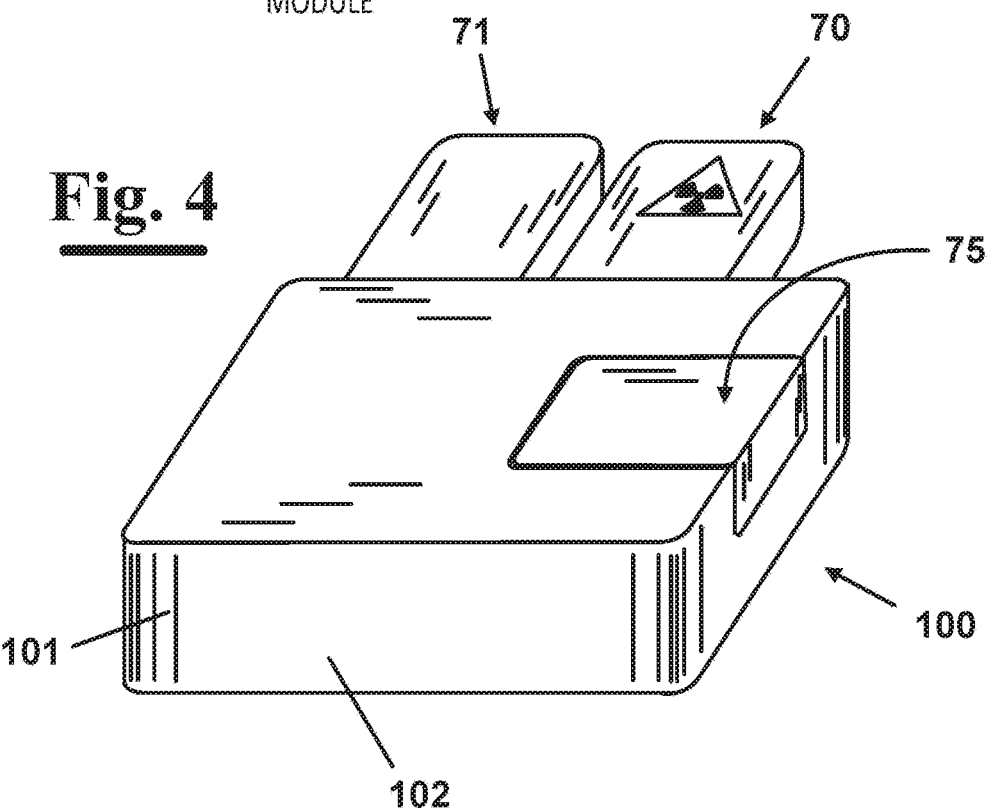

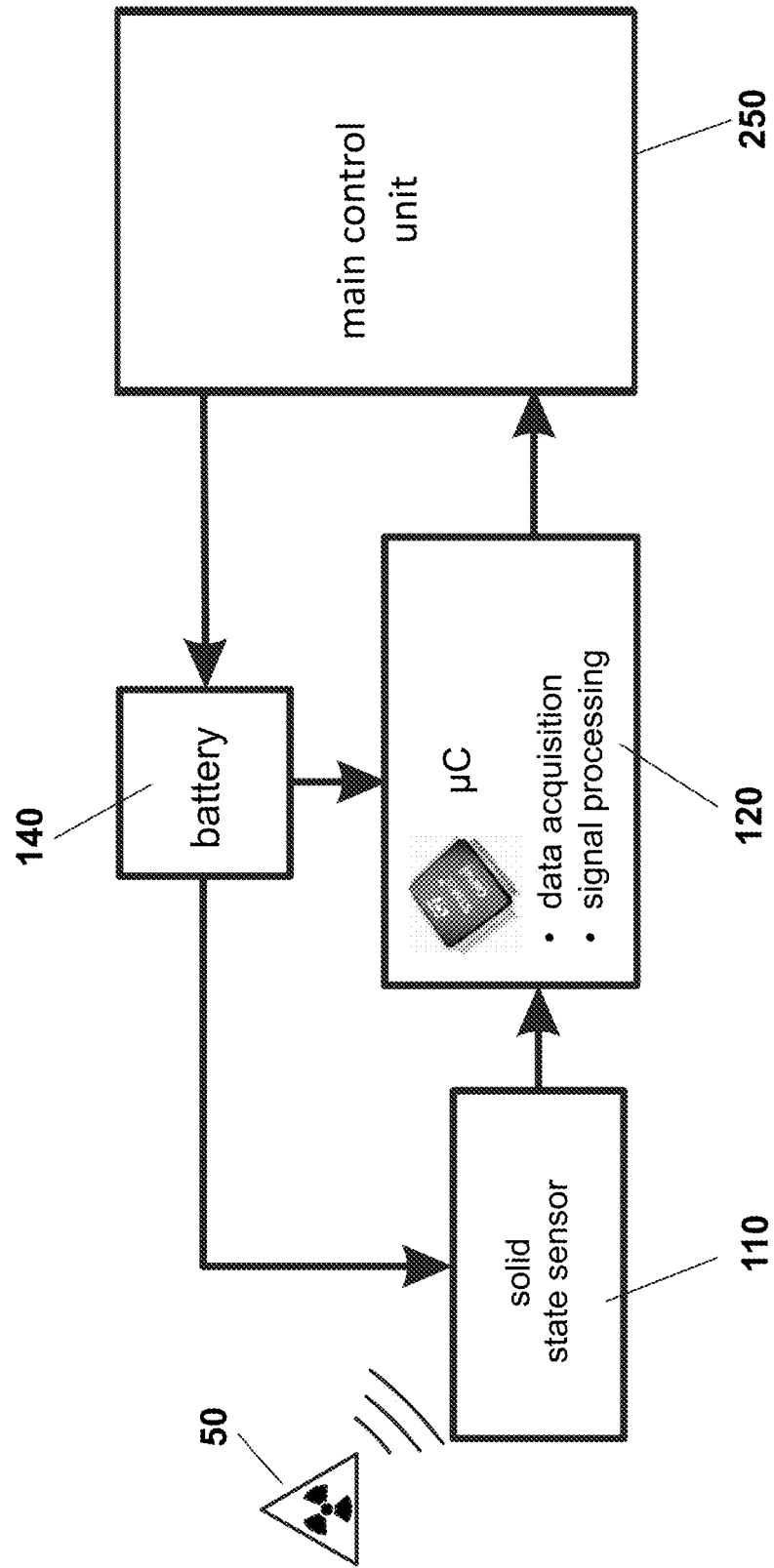

DEVICE FOR MEASURING A PLURALITY OF PARAMETERS IN PATIENT SUBJECT TO A TREATMENT WITH RADIOPHARMACEUTICALS

This application is a 371 of PCT/IB2015/051128, filed on Feb. 16, 2015, which claims priority to Italian Application No. PI2014A000013, filed Feb. 17, 2014.

FIELD OF THE INVENTION

The present invention relates to the medical field, and, in particular, it relates to a device for measuring a plurality of parameters of a patient subject to a treatment with radiopharmaceuticals.

STATE OF THE ART

As well known, substances like radiopharmaceuticals are administered to patients, usually intravenously but also orally, for diagnostic and/or therapeutic purposes.

Mainly, radiopharmaceuticals are largely used in oncology, but they are also used in cardiology and neurology, in particular for studying Parkinson and Alzheimer diseases.

Radiopharmaceuticals are molecules containing at least one radionuclide, i.e. containing radioactive isotopes. Because of radioactive isotopes, radiopharmaceuticals, once administered in a patient can be monitored from the outside, during their specific biological path, by means of specific apparatus. The instruments for detecting the activity make it possible to collect a plurality of consecutive images that depict the radiopharmaceutical distribution in the body, and show the progression of metabolism.

Normally a radiopharmaceutical has two components: the carrier, i.e. a molecule having biological functions of carrying, and the radioactive nuclide. The carrier allows guiding the radionuclide up to a target organ, or a target system. Through the use of specific diagnostic tools, the nuclides can be followed to determine the distribution of the radiopharmaceutical in the body, evaluating its affinity with target body parts and any variations of the cell biological functions. The radiopharmaceuticals of "diagnostic" type allow then localizing precisely tumour targets and deducting its biological behaviour, and then searching and starting customized therapies.

In particular, for nuclear medicine, examinations instruments are used capable of detecting the gamma radiations emitted by the nucleotides and precisely positioning the pulses responsive to their source. These instruments are called gamma cameras.

The technology of the gamma cameras has been developed progressively. From the first analogic systems, which allowed only to record planar images on a plate, recent systems have been developed that are completely digital, which carry out all the planar scintigraphic examinations, static and dynamic, and tomoscintigraphy (SPECT) of high quality and equipped with very fast and powerful processors.

The instruments that are at present available are single-headed gamma cameras for general use or multiple-headed (double, or triple headed). These are normally preferred since they are able to carry out all the scintigraphic exams, segmental planar and total body and SPECT examinations.

From the results thus obtained, it is possible to obtain morphological indications of the organs, and data on their functionality. The data that are collected by analysing the image can be used for performing a clinical diagnosis.

The patients to whom the radiopharmaceuticals have been administered, must remain in insulation for a certain number of days, usually from one to five days, and during their hospitalization they cannot come into contact with their relatives, in particular children and people who are not in perfect health conditions since the radiopharmaceutical is gradually swallowed from the body and therefore the patient's body continues to emit radiations for a determined time from the supply of the same. During the insulation period only the qualified staff of the structure where the patient is hospitalized, i.e. doctors and nurses, have access to the protected chambers of staying in hospital. The radiopharmaceutical is gradually eliminated from the patient's body also owing to its radioactive decay. During the period of time of its decay, small amount are eliminated through the sweat and through the micturition.

During this period of insulation, the patient is monitored, in such a way to be sure that the radiopharmaceutical is correctly disposed from his/her body and that then he/she is discharged from the structure in which it is hospitalized. Presently, the monitoring of the patient provides some periodic visits that are carried out by a staff member, a nurse, or a doctor, who measures the radiations emitted by the patient's body using a radiation dosimeter, usually a portable Geiger counter. More in detail, at present, in order to carry out the measurements, the staff uses a probe that positions at a certain distance from the patient's body, usually 1.0 m-1.5 m for safety reasons.

This represents a first limit of this type of detection. In fact, as well known, the intensity of the radiations decreases with the square of the distance. Therefore, this type of procedure is not capable of ensuring a high level of precision in the measuring.

In addition, in order to avoid that the staff can absorb high amount of radiations, it is necessary to limit to one, two times a day this type of detection. Since the staff members have to check and monitor also other parameters such as arterial pressure, temperature, cardiac frequency, ECG, etc. it is clear that in order to limit the contact of the staff members to the radiations a lot of people have to be involved, or, if this is not possible, the number of the daily detections has to be reduced.

Therefore, the available data for foreseeing the time of discharge of the patient are few. This makes the forecast not much reliable and, therefore, the time of hospitalization is precautionarily extended and the patient is discharged only when the measured data ensure that the decay proceeding of the radiations is below a predetermined threshold level calculated through tables and statistic measurements.

For example, in order to increase the number of available data and, therefore to have a more precise picture of the situation, environmental radiation detectors can also be used, i.e. configured to measure the trend of the radiation decay in the room in which the patient is hospitalized.

A further drawback of the difficulty of determining when the patient subject to treatment with radiopharmaceuticals can be discharged is that it is not possible to optimize the management of the insulation chambers and, then, to extend the waiting time for the patients that must be subject to this type of treatment.

U.S. Pat. No. 5,007,427 describes a method and an apparatus for determining the exact position of the left ventricle of the heart of a patient. In particular, a device provides monitoring the heart arranged on a flexible vest that is worn by the patient during the studying period. More in detail, the device for monitoring comprises a main detector of gamma rays and a secondary detector of gamma rays of the type used in the field of the nuclear medicine for monitoring, or diagnosing, the physiological activities of a patient during a predetermined period of time. The procedure described in U.S. Pat. No. 5,007,427, thus, provides to inject a radiopharmaceutical in the circulatory system of the patient to provide an output signal representative of the activity of the left ventricle of the heart. The main detector is adapted to measure the output signal for producing a signal representative of the activity with time of the left ventricle of the heart. Therefore, the system described in U.S. Pat. No. 5,007,427, is not used for determining the time of discharge of a patient subject to radiopharmaceuticals, but has a completely different object.

In WO2009/127954, in the name of the same applicant, a device is described for supporting a predetermined number of sensors of determined physiological parameters of a patient, such as the arterial pressure. However, WO2009/127954 does not provide a sensor for measuring the radiations emitted by a radiopharmaceutical, nor the document describes a criteria to establish the time of discharge of a patient subject to treatment with radiopharmaceuticals.

SUMMARY OF THE INVENTION

It is then a feature of the invention to provide a device for measuring a plurality of parameters of a patient subject to treatment with radiopharmaceuticals for carrying out measurements highly precise and ensuring a repeatability of the measure.

It is also a feature of the invention to provide such a device to avoid that qualified staff, such as nurses, can be hit by the radiations emitted by the patient's body during the detection step.

It is a further feature of the invention to provide such a device for investigating specific areas of the patient's body, in order to determine in a precise way the status of advancing of the decay of the radioactive particles at the specific investigated area.

It is a still a feature of the invention to provide such a device to overcome the difficulties of the devices of the state of the art.

These and other objects are achieved by a multi-parametric device for measuring a plurality of parameters of a patient subject to a treatment with radiopharmaceuticals, said device comprising:

a main body constrained to the patient's body, in such a way that said measurement device, in use, is worn by the patient;

a plurality of measurement modules, each measurement module of said plurality equipped with a sensor configured to measure a predetermined parameter of said patient;

a microprocessor arranged to process a plurality of data measured by said plurality of sensors obtaining a plurality of processed data;

a wireless transmission means arranged to send via wireless communication said data processed by said microprocessor to a control remote unit;

a supplier arranged to supply said microprocessor and each sensor of said plurality;

engagement means arranged to engage with respective engagement means of each measurement module of said plurality, said engagement means arranged to operatively connect said microprocessor with each sensor of said plurality;

whose main feature is that at least one measurement module of said plurality is a measurement module of radiations equipped with a radiation sensor configured to measure said radiations in a predetermined time range Dt;

and that said measurement module is configured to arrange at a short distance from the patient's body in such a way that said radiation sensor is arranged to measure the radiations emitted by the radiations source from a short and substantially fixed distance;

and that said control unit is arranged to carry out a processing procedure of the processed data for determining the time of discharge of the patient subject to the pharmacological treatment.

The technical solution provided by the present invention of using a multi-parametric device avoids that medical, or paramedical, staff enters frequently in the room where the patient is hospitalized for carrying out the measurement of the parameters to be monitored such as arterial pressure, temperature, cardiac frequency, etc. This way, therefore, it is avoided that the staff can be repeatedly hit by the radiations emitted by the patient's body. Furthermore, the possibility to avoid the use of medical and paramedical staff for carrying out the measurements carries out frequently such detection without the drawback to put to risk the safety of the staff.

In particular, the radiation sensor is adapted to emit an impulse, or "spike", for each detection of radiations emitted by the patient. More in detail, the radiation sensor emits a pulse when detects a radiation associated with an energy higher than a predetermined value.

In particular, the microprocessor, operatively connected to the sensor, is adapted to count the number of pulses emitted by the radiation sensor in a predetermined time range Dt1 obtaining the number of pulses in time range n(Dt1).

Then, the number of pulses $n(Dt_1)$ that have been counted by the microprocessor is sent to the remote control unit by the wireless transmission. The control unit is adapted to associate a point $P(Dt_1)$ responsive of the number of pulses $n(Dt_1)$ on a diagram $n(Dt_1)$ versus time (t). The above described succession of steps is repeated a predetermined number of times up to cover a predetermined time of observation. More in detail, once that the overall time of observation $t_{tot}$ has benne decided, for example 24 hours, and the detection time $Dt_1$, the time range $Dt_2$ between a detection and the following one is established. For each range Dti the number of pulses emitted by the radiation sensor is calculated when radiations higher than a predetermined energy value are detected and plotted on a diagram.

In particular, the control unit is arranged to carry out a processing procedure comprising the steps of:

constructing a characteristic curve g representative of the number of radiations detected by said sensors of radiations in function of the time;

determining the time t at which said curve g assumes a value equal, or lower, than a predetermined lower threshold value t*, said time t corresponding to the time of discharge of the patient.

In particular, the construction of the characteristic curve g provides the steps of:

counting the number of pulses emitted by said radiation sensor to detect said radiations in a predetermined time range Δt1 obtaining the number of pulses in said time range n(Δt1);

identifying a point representative of said number of pulses n(Δt1) on a diagram n(Δt1) versus time (t);

repeating said counting step and said identifying step for a predetermined number k of time ranges Dt1 spaced from the following of a second predetermined time range $Dt_2$ for an overall time of detection $Dt_{tot}$, at the end of said repeating step being determined of the number k of particles radioactive in a predetermined time range $n_i(Dt_1)$, with $i=1 \ldots k$ and defined on said graph a corresponding number k of points Pi;

constructing on said graph said characteristic curve g through said plurality of points Pi, each point Pi of said plurality corresponding to a number of pulses $n_i(Dt_1)$ counted at the i-th second time range $Dti_2$;

determining said time of discharge td of the patient from said characteristic chart g, through the steps of:

comparing said characteristic chart g built with a plurality of predetermined calibration curve;

selecting among said plurality of calibration curve of the curve g* that better approximates said built characteristic chart g;

identifying on said selected calibration curve g* the time t at which said curve g* assumes a value equal, or lower, than said predetermined lower threshold value $n^*(Dt_1)$.

Advantageously, the engagement means of each measurement module and the engagement means of the main body are adapted to provide a matching form. In particular, the engagement means is configured to recognizing each module.

In particular, in addition to the measurement module of the radiations emitted by the patient's body, at least one measurement module is provided selected from the group consisting of:

a measurement module configured to measure the arterial pressure;

a measurement module configured to measure the cardiac frequency;

a measurement module configured to measure SpO2;

a measurement module configured to measure the position;

a measurement module configured to measure the temperature;

a measurement module configured to measure the ECG 4 derivations;

a measurement module configured to measure the breath frequency;

or a combination thereof.

Advantageously, the control unit is adapted to carry out a digital filtering of said plurality of data transmitted via wireless communication by said microprocessor. This way, it is possible to reduce, through a digital filtering, noises of the signal, i.e. the possible distortion owing to the wireless transmission.

Advantageously, the measurement module of the radiations has a shielding element arranged to insulate said radiation sensor from said wireless transmission means. In fact, the wireless transmission could interfere with the detection of the radiations by the radiation sensor. Instead, the technical solution of providing the shielding element makes it possible to insulate the sensor from the wireless transmission means and therefore to avoid said drawbacks.

In particular, the shielding element is a thin plate of predetermined thickness of a metal material, for example aluminium.

Preferably, the radiation sensor is a solid state sensor. Such a solution allows reducing its size and ensuring in the meantime precise measurements of the energy associated with the radiations emitted by the patient's body. Therefore, the choice of using a solid state sensor is particularly advantageous in the case of a measurement device of wearable type.

In a advantageous exemplary embodiment the measurement device comprises:

a first measurement module of radiations, said measurement module equipped with a first radiation sensor configured to measure a first plurality of radiation data at a first analysis zone of the patient's body;

at least a second measurement module of radiations, said second measurement module equipped with a second radiation sensor configured to measure a second plurality of radiation data at a second zone of analysis of the patient's body.

This exemplary embodiment allows, in particular, of monitoring with a single multi-parametric device the radiations emitted by the patient's body in two different points, in particular at a first organ and a second organ of the patient, for example at the thyroid and the liver. This way, it is also possible to evaluate if the radiations induced by the radiopharmaceutical involves in addition to the element subject to treatment with radiopharmaceuticals also other areas, i.e. organs, or tissues of the patient's body, by the measurement of the radiations emitted near the parts of interest. This allows to have a more complete picture of the physical conditions of the patient.

According to another aspect of the invention a measurement module of the radiations emitted by the body of a patient subject to treatment with radiopharmaceuticals, said modular portion comprises:

a radiation sensor configured to measure said radiations in a predetermined time range;

engagement means arranged to engage said module to respective engagement means of a multi-parametric modular device, said multi-parametric modular device being configured to be worn by a patient in such a way that said radiation sensor is adapted to measure the radiations emitted by the patient's main body maintaining substantially fixed the distance from the source of radiations, said multi-parametric modular device comprising:

a microprocessor configured to process said plurality of radiation data measured by said measuring module obtaining a plurality of processed data;

wireless transmission means arranged to send via wireless communication said data computed by said microprocessor to a remote control unit;

a supplier arranged to supply said microprocessor and said radiation sensor.

Advantageously, the multi-parametric measurement device comprises a display on which are displayed the main parameters measured by the sensors to it connected.

In particular, it is possible to provide a plurality of measurement modules of radiations of different type. In particular, each measurement module of the radiations is equipped with a sensor of different type, i.e. sensitive to a predetermined range of radiations. For example, a criteria that can be used for selecting a measurement module of the radiation with respect to another can be to evaluate which radiopharmaceutical has been used. In function of the radiopharmaceutical that has been used, in fact, the radionuclide incorporated in it, i.e. the radioactive isotope, has a predetermined time of decay and firstly emits radiations in a specific range of energy. Therefore, the radiation sensor is selected on the basis of the type of radiopharmaceutical used.

According to a further aspect of the invention, a measurement device of radiations emitted by the body of a patient subject to treatment with radiopharmaceuticals is configured to can be of a type wearable and provides:

a solid state radiation sensor configured to measure the radiations in a predetermined time range and to provide a corresponding plurality of radiation data;

a microprocessor configured to process said plurality of radiation data measured by said sensor obtaining a plurality of processed data.

Advantageously, a transmitting means is also provided pf wireless type arranged to send through wireless communication said data computed by said microprocessor to a remote control unit.

Furthermore, the device provides a supplier arranged to supply the microprocessor and the radiation sensor.

In particular, a support can be provided for the measurement device arranged to be constrained to the patient's body and then of making the measurement device of the radiations of wearable type as described above.

BRIEF DESCRIPTION OF THE DRAWINGS

The invention will be now shown with the following description of its exemplary embodiments, exemplifying but not limitative, with reference to the attached drawings in which:

FIG. 1B diagrammatically shows a first exemplary embodiment of a multi-parametric device, according to the invention, for measuring a plurality of parameters of a patient subject to treatment with radiopharmaceuticals;

FIG. 3 diagrammatically shows a top plan view of a possible exemplary embodiment of the multi-parametric device of FIG. 1B;

FIG. 4 shows the device multi-parametric of FIG. 3 a perspective view of;

FIG. 5 diagrammatically shows a block diagram in which the main components are indicated of the multi-parametric device according to the invention;

DETAILED DESCRIPTION OF THE INVENTION

Figure 1A:
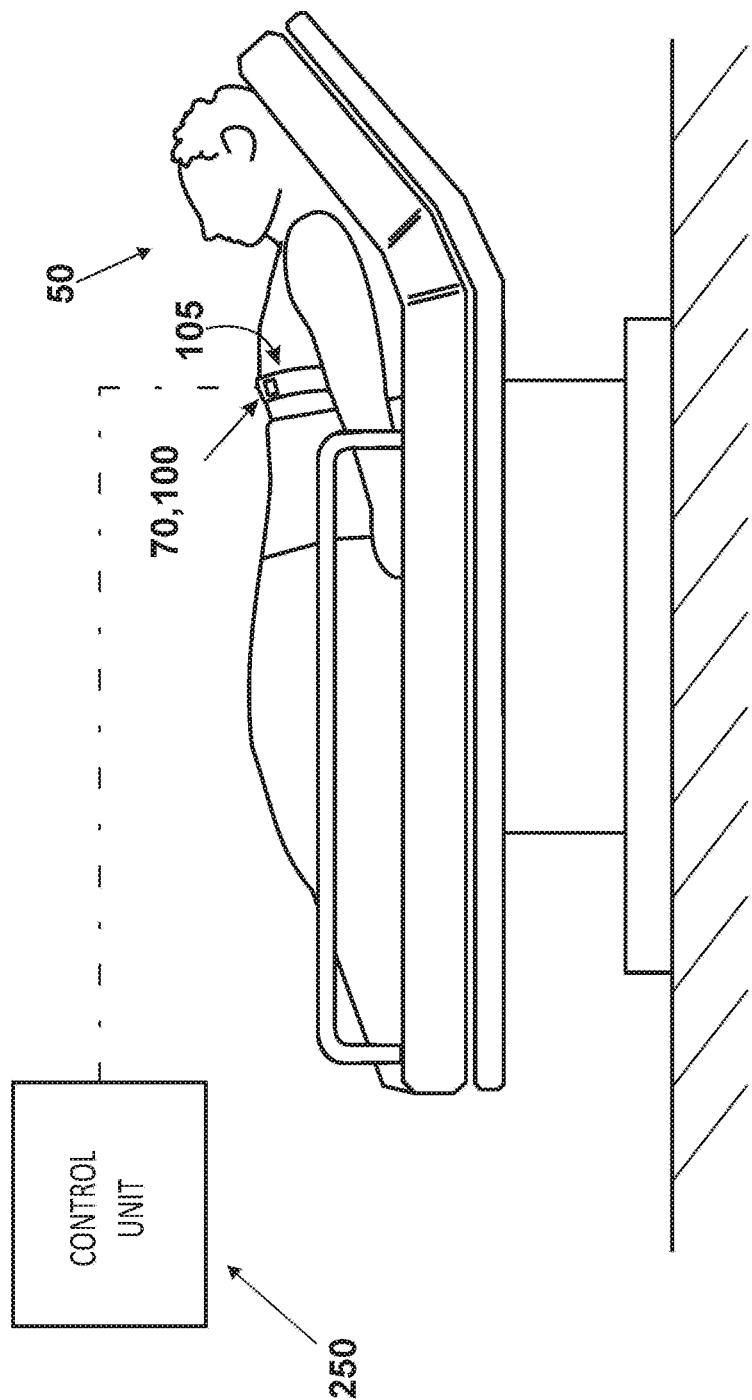
FIG. 1A diagrammatically shows a first exemplary embodiment of a wearable device, according to the invention, for measuring radiations emitted by a patient subject to treatment with radiopharmaceuticals.
Figure 2A:
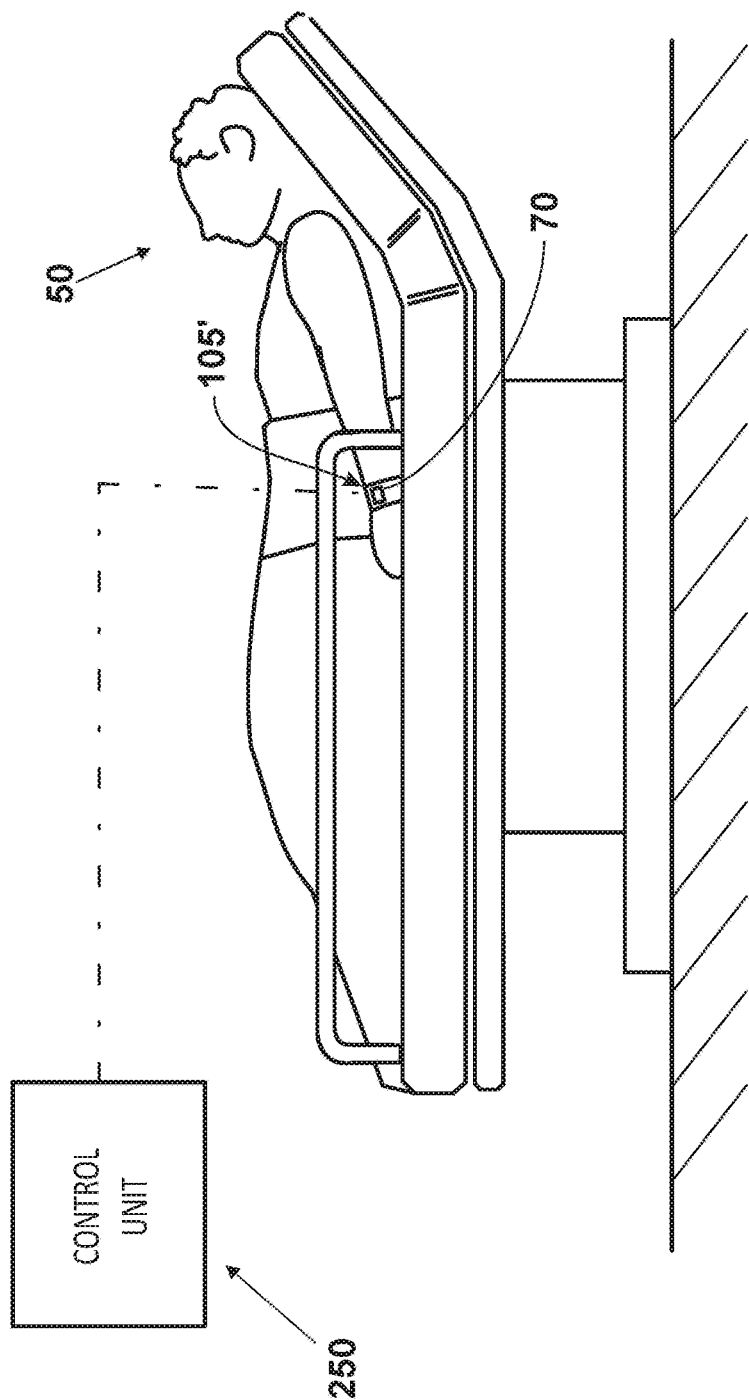
FIG. 2A diagrammatically shows an exemplary embodiment of the device of FIG. 1A.

With reference to FIGS. 1A and 2A, a measurement device 70 for measuring the radiations emitted by the body of a patient 50 subject to a treatment with radiopharmaceuticals is configured in such a way that it can be of wearable type and comprises, in particular, a solid state radiation sensor 110 configured to measure the radiations in a predetermined time range and to provide a corresponding plurality of radiation data. Furthermore, a microprocessor 150 is provided configured to process the above described plurality of radiation data that have been measured by the sensor 110 obtaining a plurality of processed data. The invention provides, advantageously, transmission means of wireless type arranged to send via wireless communication the above described data processed by the microprocessor 150 to a remote control unit. Furthermore, the device 70 provides a supplier arranged to supply the microprocessor 150 and the solid state radiation sensor 110. In particular, a support 105 can be provided for the measurement device 70 arranged to be constrained to the patient's body and then to make the measurement device of radiations of wearable type as above described.

Figure 2B:
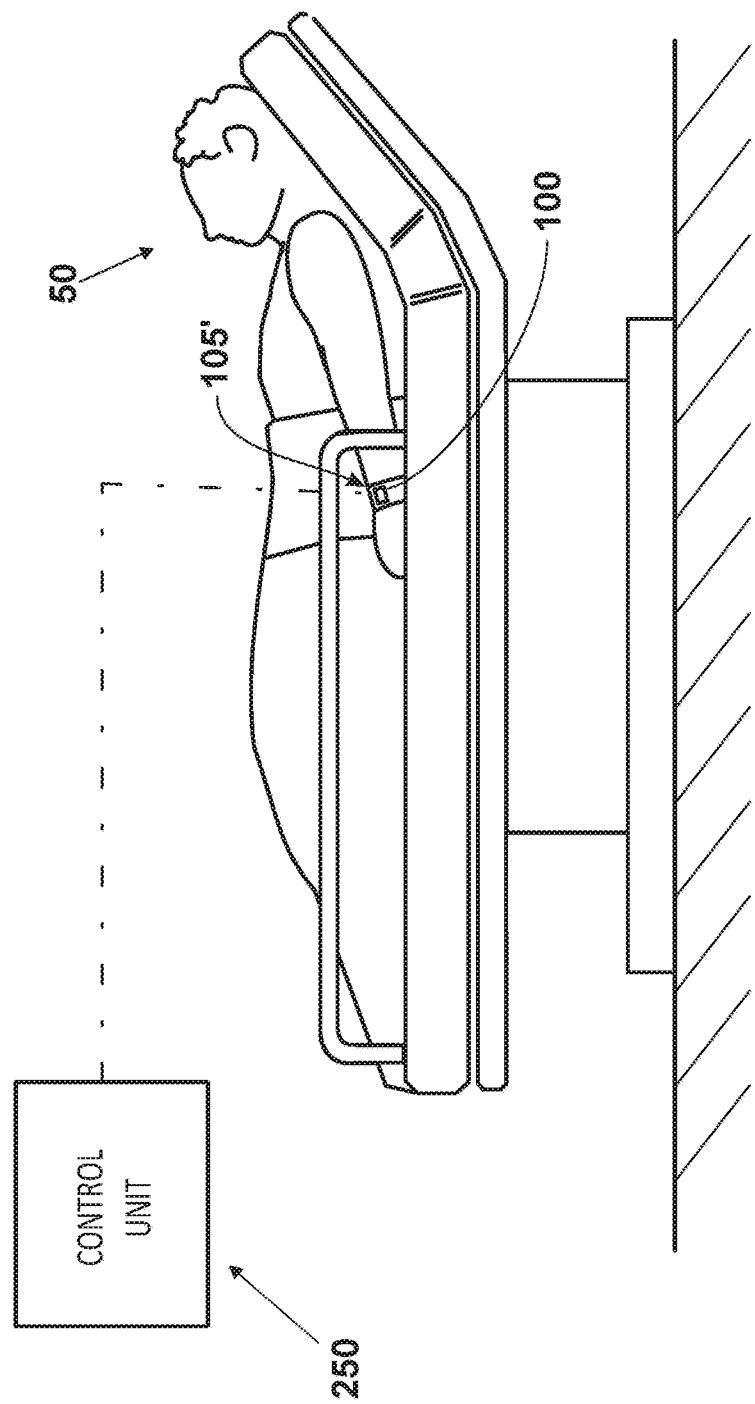
FIG. 2B diagrammatically shows an exemplary embodiment of the multi-parametric device of FIG. 1B.
Figure 6:
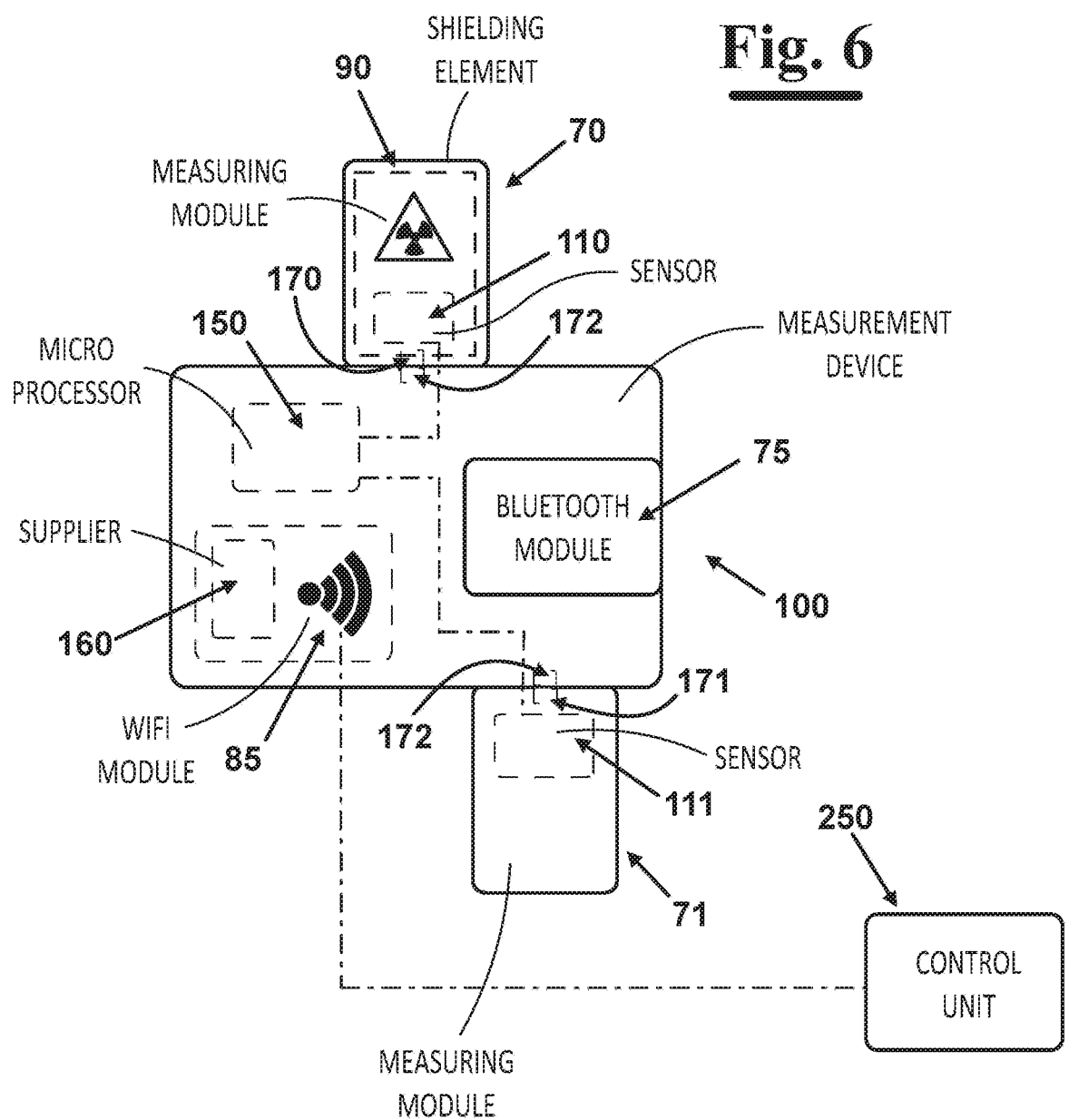
FIGS. 6 and 7 show in top plan views two possible exemplary embodiments of the invention of FIG. 3.
Figure 7:
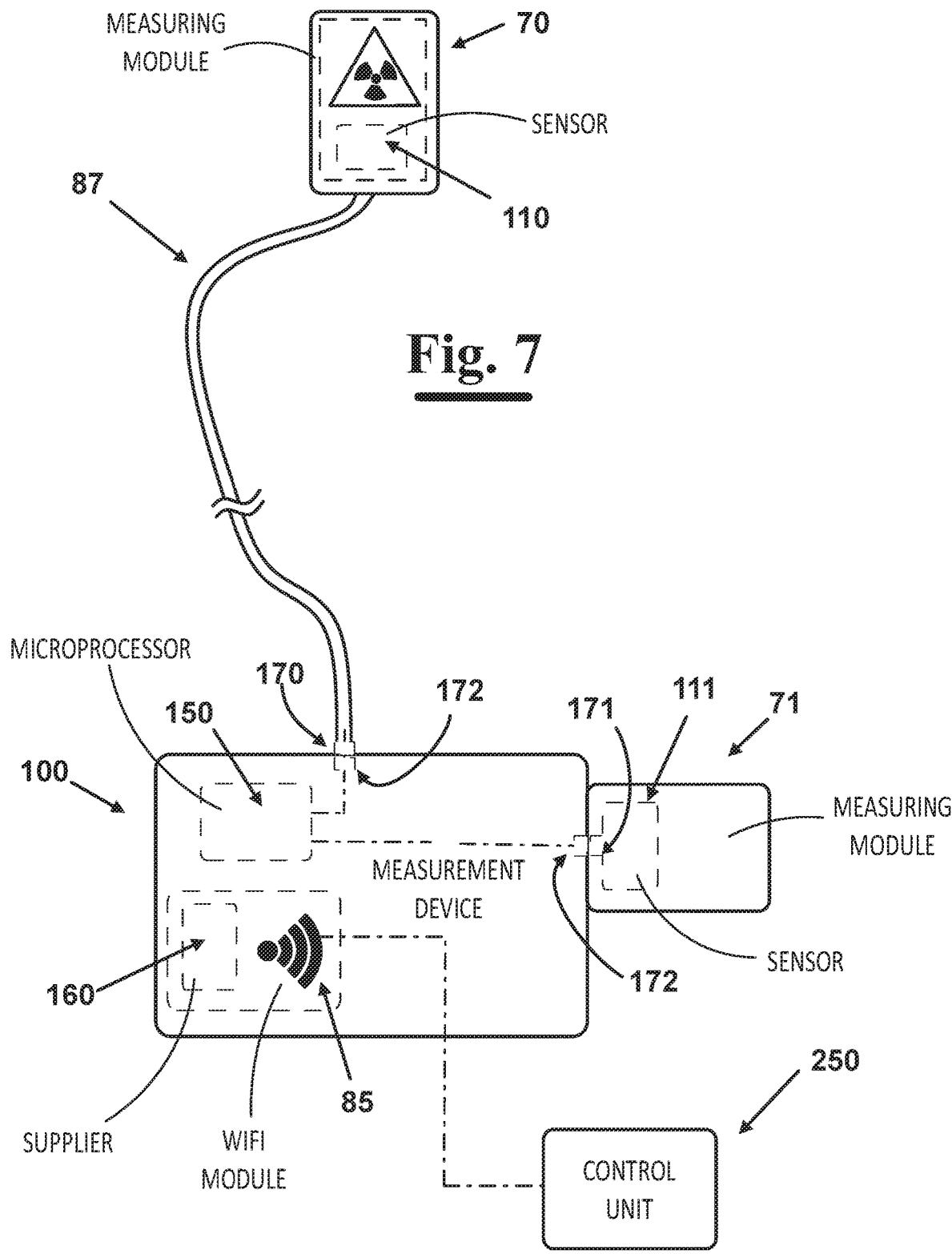

As shown in detail in FIGS. 1B, 2B, 3 and 4, said measurement device 70 of radiations can be advantageously configured as a module of a multi-parametric device 100 for measuring a plurality of parameters of a patient subject to a treatment with radiopharmaceuticals. More in detail, the multi-parametric device, thus obtained, comprises a main body 101 constrained to the patient's body 50 in such a way that the measurement device 100 is of wearable type. For example, the main body 101 can comprise a box-like body 102 mounted on a belt 105 that is constrained to the thorax of the patient 50 (FIG. 1B), or on a bracelet 105' that is constrained to the wrist of the patient 50 (FIG. 2B).

As shown in detail in FIGS. 3 and 4, the device 100 comprises a plurality of measurement modules, for example a first module 70 and a second module 71, each of which has a respective sensor 110, 111, configured to measure a predetermined parameter of the patient 50. Even though in FIGS. 3 and 4 the two measurement modules 70 and 71 are shown connected to a same side of the measurement device 100 it is however also provided that the same modules can be arranged on different sides of the main body 101. Therefore, the device 100 is a multi-parametric device of modular type.

The device 100 is also provided with a microprocessor 150 configured to process a plurality of data measured by the plurality of sensors 110, 111, obtaining a plurality of processed data. Furthermore, a transmission means is furthermore provided of wireless type arranged to send via wireless communication the data processed by the microprocessor 150 to a remote control unit 250. For example, the wireless transmission can be made by means of a Bluetooth module 75 and/or a wifi module 85, or other types of wireless communication. Furthermore, it is provided a supplier 160, for example a rechargeable battery, arranged to supply the microprocessor 150, each sensor 110, 111, and other electronic components.

In particular, each measuring module 70, 71 engages with the main body 102 by engagement means 170, 171 arranged to engage with respective engagement means 172 of the hollow container body 102. More in detail, the engagement means 170, 171 and 172 are adapted to operatively connect the microprocessor 150 with each sensor 70, 71 engaged to the main body 102. The engagement means 170,171 and 172 can be electric connection elements of known type.

According to the invention, the device 100 provides at least one measurement module of radiations 70. This is equipped with a sensor of radiations 110 configured to measure the radiations emitted by the patient's body in a predetermined time range Dt.

The radiation sensor 110 is preferably a solid state sensor. Such solution allows to reduce its size and to ensure, in the meantime, precise measurements of the energy associated with the radiations emitted by the patient's body. Therefore, the choice of using a solid state sensor is particularly advantageous in case of a measurement device of wearable type.

The basic idea of the present invention, i.e. of using a measurement module 70 of radiations connected to the main body 102 constrained to the patient's body 50 allows to carry out a detection from a short distance from the patient's body 50. Therefore, the radiation sensor 110 is adapted to measure the radiations emitted by the source of radiations from a short distance and substantially fixed and therefore highly precise, which is localized and reliable. In fact, as well known, the radiation energy is in inverse relation with the square of the distance. Therefore, reducing, with respect to the prior art devices, the distance between the radiation detector and the source of radiations, i.e. the patient's body 50 treated with radiopharmaceuticals, it is possible to increase the precision level of the measurement.

Still according to the invention, in addition to the measurement module of the radiations 110 emitted by the patient's body 50, at least one measurement module is provided selected from the group consisting of: a module for measuring the arterial pressure, a module for measuring the cardiac frequency, a module for measuring SpO2, a module for measuring the position, a module for measuring the temperature, a module for carrying out the ECG, in particular ECG 4 derivation, a module for measuring the frequency breath or any combination thereof. The technical solution provided by the present invention of using a multi-parametric device 100 avoids that medical, or paramedical, staff enters frequently in the room in which the patient is hospitalized for carrying out the measurement of the parameters to be monitored such as arterial pressure, temperature, cardiac frequency, breath frequency etc. This way, therefore, it is avoided that the staff are repeatedly hit by the radiations emitted by the patient's body. Furthermore, the possibility to avoid the use of medical and paramedical staff for carrying out the measurements carries out frequently such detection without the drawback to put in risk the safety of the staff.

More in detail, the radiation sensor 110 is adapted to emit an impulse, or "spike", at each detection of radiations emitted by the patient 50. More in detail, the radiation sensor 110 emits a pulse when it detects a radiation associated with an energy higher than a predetermined value. The microprocessor 150, operatively connected to the sensor 110, is adapted to carry out a count of the number of pulses emitted by the radiation sensor 110 in a predetermined time range Dt1 obtaining the number of pulses emitted by the sensor 110 in the considered time range $n(Dt1)$.

Then, the number of pulses $n(Dt_1)$ counted by the microprocessor 150 is sent to the remote control unit 300 from the above described wireless transmission, for example by means of Bluetooth, or wifi. The control unit 250 is adapted, in particular, to associate a point $P(Dt_1)$ representative of the number of pulses $n(Dt_1)$ on a diagram $n(Dt_1)$ versus time (t). The above described succession of steps is repeated a predetermined number of times up to cover a predetermined time of observation. More in detail, once the overall time of observation $t_{tot}$ has been decided, for example 24 hours, and each time of detection $Dt_1$, the time range $Dt_2$ between a detection and the subsequent one is decided. For each time range $Dt_1$ the number of pulses emitted by the radiation sensor 110 is computed when radiations are detected that are higher than a determined energy and reproduced on a graph. An example of a graph obtainable through the above described processing is diagrammatically shown in FIG. 8. A further advantage of the present invention is that it is possible to carry out many measurements, in particular in predetermined instants, and in such a way to have a repeatability of the measure that further increases the reliability of the measure and then of the estimate of the time of discharge of the patient that has been measured through the procedure above described.

The mutual engagement means 170, 171 of each measurement module 70, 71 and the mutual engagement means 172 of the main body 102 can be arranged to provide a positive engagement. In particular, the engagement means can be configured to be capable of recognizing each module, i.e. to avoid an engagement between a module and the main body 101 at a wrong connection port, i.e. not adapted to operatively connect the module connected with the main body to the microprocessor. This can be obtained through mutual engagement means that is arranged to provide a positive engagement between the module and the main body. In this case the mutual engagement means 170, 171 and 172 in addition to ensure an electric connection between each sensor 110, 111 and the microprocessor 150 are also adapted to ensure that the mechanical connection between each module 70, 71 and the main body 101 of the multi-parametric device 100 occurs correctly. This can be made for example as described in WO2009127954 in the name of the same applicant. The engagement means 172 can be configured to recognize the module 70,71, i.e. to avoid that a module 70,71 is connected to the main body 101 at a wrong connection port.

According to an exemplary embodiment, the control unit 250 can carry out a digital filtering of the data transmitted via the above described wireless communication. This way, it is possible to reduce through a digital filtering noises of the signal, i.e. the possible distortion delivered during the wireless transmission. In particular, the digital filtering is adapted eliminate the irregular spike, i.e. not corresponding to an event really occurred, in other words to a detection of radiations by the radiation sensor 110, but to a noise produced by the interference with the signal of the wireless transmission.

In addition, or alternatively, to the digital filtering, in order to remedy said disadvantage, i.e. the interference between the signal of the wireless transmission and the detection of the radiations by the sensor 110, the module 70 can be equipped with a shielding element 90 arranged to insulate the radiation sensor 110 from the wireless transmission means. Such a solution provides then to interpose a physical barrier between the radiation sensor 110 and the antenna that transmits the data wirelessly. The shielding element 90 can be a thin plate of predetermined thickness of a metal material, for example aluminium.

Figure 8:
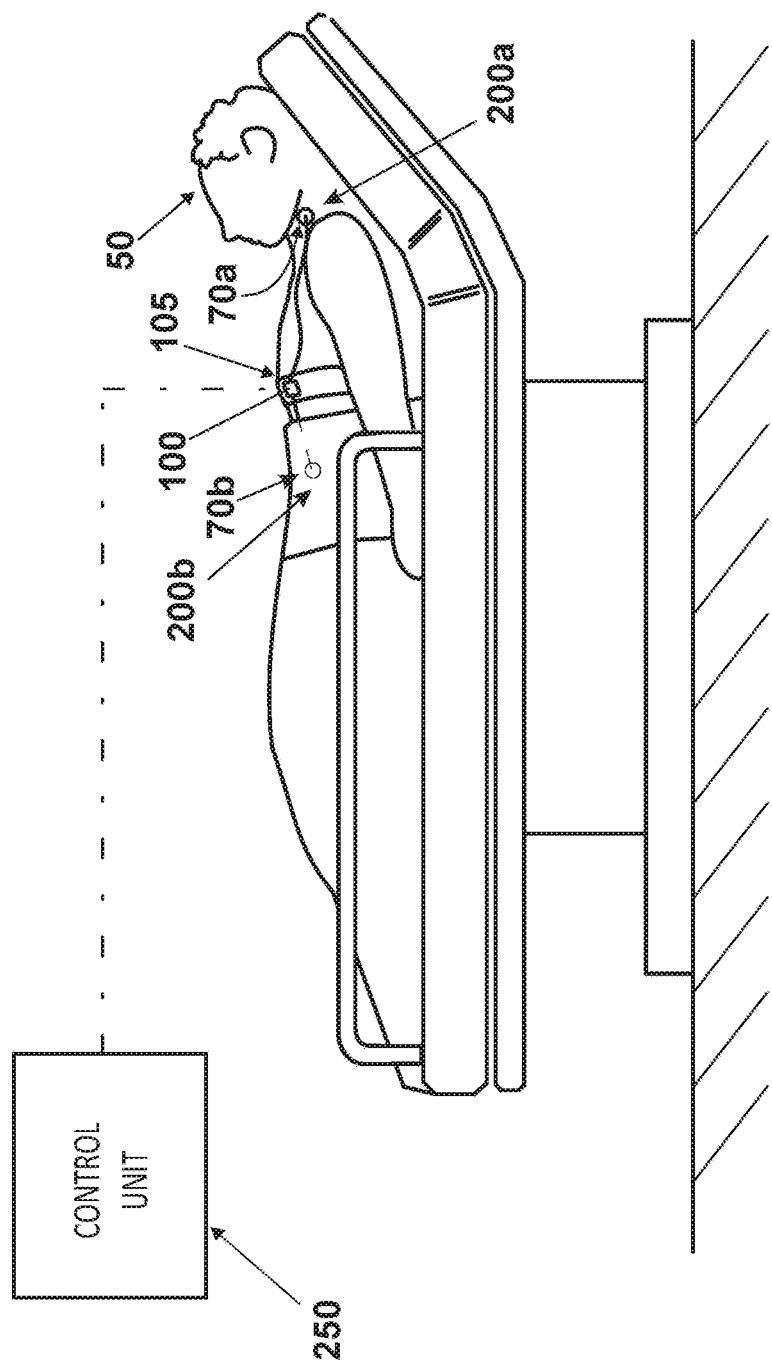
FIG. 8 diagrammatically shows a further exemplary embodiment of the device of FIG. 1B applied to a patient.
Figure 9:
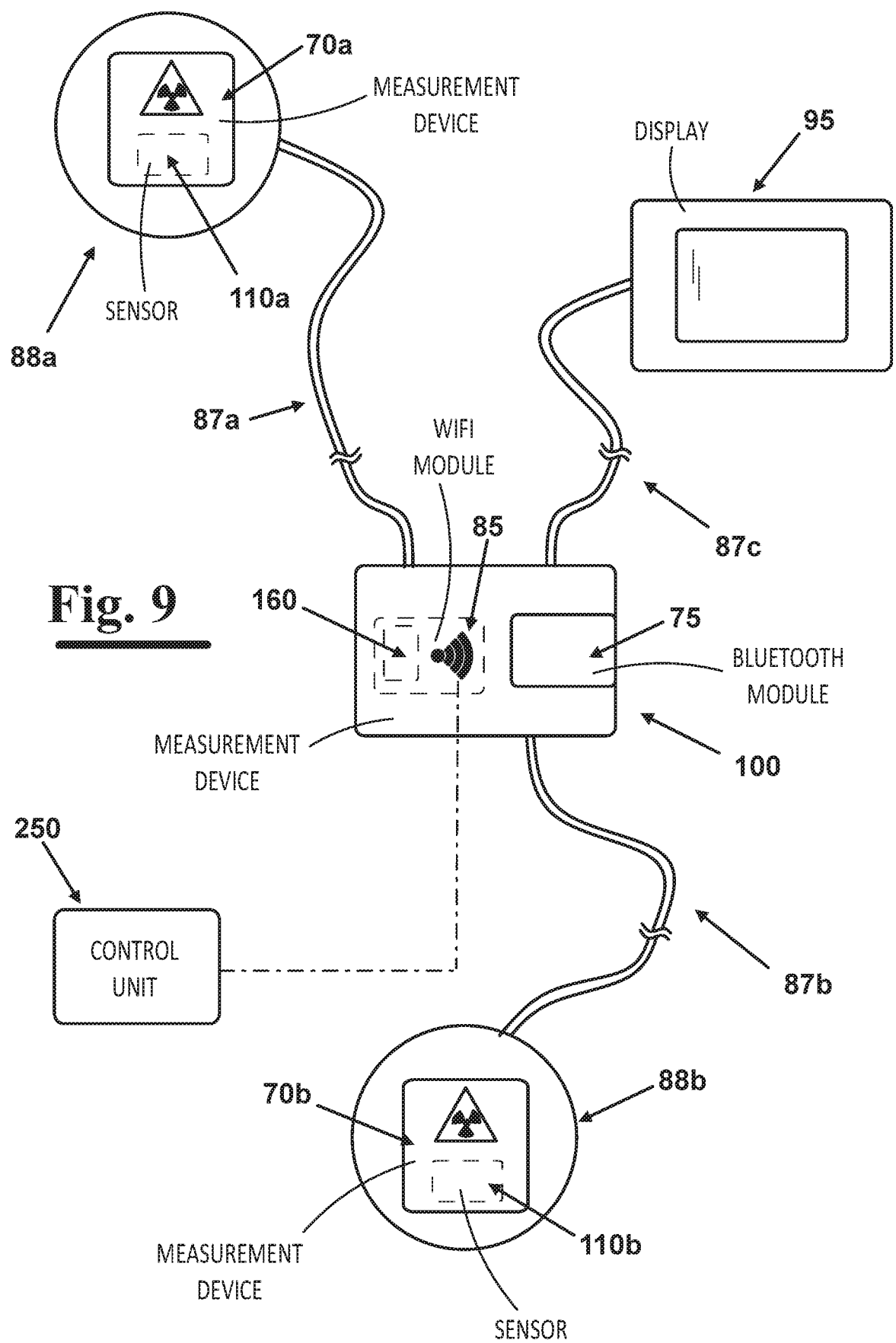
FIG. 9 shows the exemplary embodiment of FIG. 8 in a top plan view of highlighting some technical features.

As diagrammatically shown in FIGS. 8 and 9, in a advantageous exemplary embodiment, the measurement device 100 comprises a first measurement module 70*a* of the radiations and at least one second measurement module 70b of the radiations. Each measurement module 70a, 70b, is equipped with a respective radiation sensor 110a and 110b. More in detail, the sensor 110a is adapted to measure a first plurality of radiation data at a first zone of analysis 200a of the patient's body 50, for example in the zone surrounding the carotid. The second module 70b equipped with a second radiation sensor 110b is, instead, configured to measure a second plurality of radiation data at a second zone of analysis 200b of the patient's body 50, for example at the liver. In this exemplary embodiment, each measurement module 70a, 70b, is advantageously connected to the main body 102 and after microprocessor 150 by a respective connection cabled 87a, 87b. In this case each module 87a, 87b can be provided mounted to an adhesive element, for example a suction cap 88a, 88b, of the type used for ECG, in such a way to be engaged at the respective area of analysis 200a, 200b.

This exemplary embodiment allows, in particular, to monitor with a single multi-parametric device 100 the radiations emitted by the patient's body in two different points. This way, it is also possible to consider if the radiations induced by the radiopharmaceutical in the patient involves, in addition to the organ subject to treatment with radiopharmaceuticals, also other areas, i.e. other organs, or tissues of the patient's body, by the measurement of the radiations emitted near the interested parts. This way, it is possible to have a more complete picture of the physical conditions of the patient.

The multi-parametric measurement device 100 can also have a display 95 on which the main parameters measured by the sensors 110, 111 to it connected are displayed. Even though in FIG. 10 the display 95 is shown connected by a wire 87c to the main body 102 it is also provided that it can be integrated in the main body 102 same.

With reference to the block diagram 300 of FIG. 10, the measurement device of wearable type 100, according to the present invention as described with reference to FIGS. 1 to 10, can be used for determining the time of discharge of a patient 50 subject to a treatment with radiopharmaceuticals.

Figure 10:
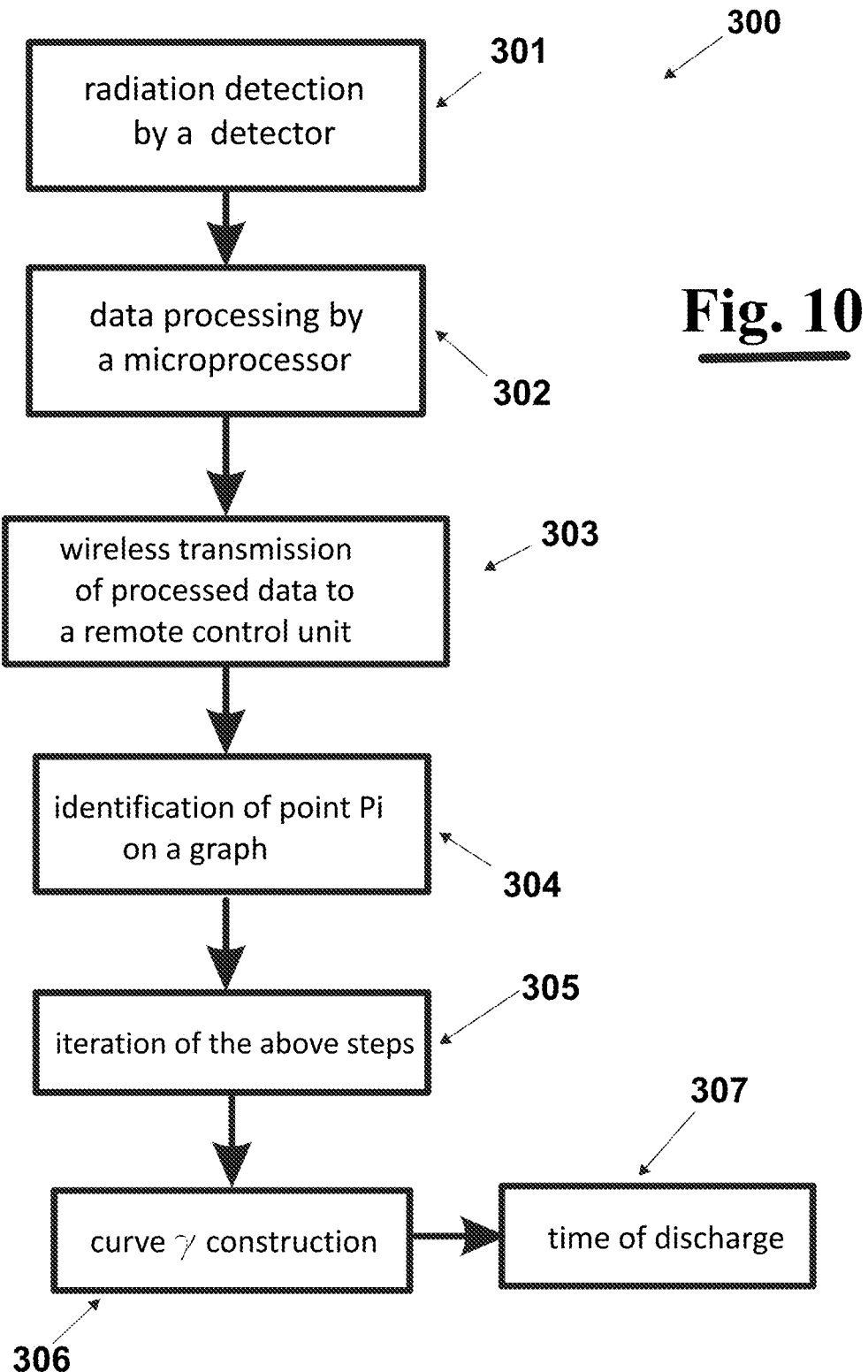
FIG. 10 shows a block diagram of a procedure that can be carried out with the device according to the present invention in order to determine in how long time the patient disposes the radiopharmaceutical and then can be discharged from the building where it is hospitalized.

More in detail, as shown with reference to the scheme 300 of FIG. 10, a detecting step is provided by the radiation sensor 110 of the radiations emitted by the patient's body 50 in a first predetermined time range $Dt_1$ obtaining a plurality of measured data, block 301.

The detected data are then processed by a microprocessor 150 that carries out the counting of the number of pulses emitted by the detector device when the radiations in a first predetermined time range Dt: are detected, block 302. More in detail, if the first time range Dt: is chosen equal to 1 minute, the number of pulses $n(Dt_1)$ is expressed in c.p.m., i.e. "count for minute", or equivalent counts. In practice the number of pulses in said time range corresponds to the energy associated with the detected radiations. As described above, each datum detected by the radiation sensor 110 and processed by the microprocessor 150 is sent via wireless communication to a control unit 250, block 303. The control unit 250 provides then to plot the received processed data on a graph (number of pulses vs time) identifying a corresponding point Pi, block 304 (see for example FIG. 11).

The detecting and processing steps are then repeated for a predetermined number k of time range Dt1 with a delay of a second predetermined time range $Dt_2$ from the following one for a predefined overall time of observation $t_{tot}$, block 305.

At the end of the iteration a predetermined number k of numbers of pulses is determined in each predetermined time range $ni(Dt_1)$, with i=1 . . . k and then a corresponding number k of points Pi is identified on the graph.

Once the above described k points Pi have been identified it is possible to proceed with the construction on the graph of a characteristic chart g, block 306. By the characteristic chart g it is possible to determine the time of discharge td of the patient. More in detail, the determination of the time of discharge td can be carried out identifying on the graph on which the characteristic chart g has been reproduced, a lower threshold value $n*(Dt_1)$ and then from the curve g the time of discharge t* that corresponds to the time t at which the curve g assumes a value equal, or less than said lower threshold value. An example of this procedure is diagrammatically shown in FIG. 11.

The above disclosed lower threshold value can be for example determined through a comparison, for example carried out by the control unit 250, of the characteristic chart g constructed with a plurality of predetermined calibration curve loaded in a special database. Between the above described plurality of calibration curve is selected the curve g* that better approximates the constructed characteristic chart g. At last, on the above described calibration curve g* the time t is selected at which the curve g*, and then within a certain margin of uncertainty also the curve g, assumes a value equal, or lower, than the predetermined lower threshold value $n*(Dt_1)$.

More in detail, the calibration curve loaded in the database are curve constructed using known coefficient, i.e. parameters. The coefficient to be considered can be weight of the patient, age of the patient, type of radiopharmaceutical that has been used, type of diseases of the patient, or more in general a combination of these parameters. Therefore a first selection of the calibration curve that can be used is carried out on the basis of the identity, or the likeness, of the values of the above described parameters, or coefficient, with those of the patient. Then, among the curves that have passed the first selection it is selected the curve that has a trend similar to that one of the characteristic chart g.

Figure 11:
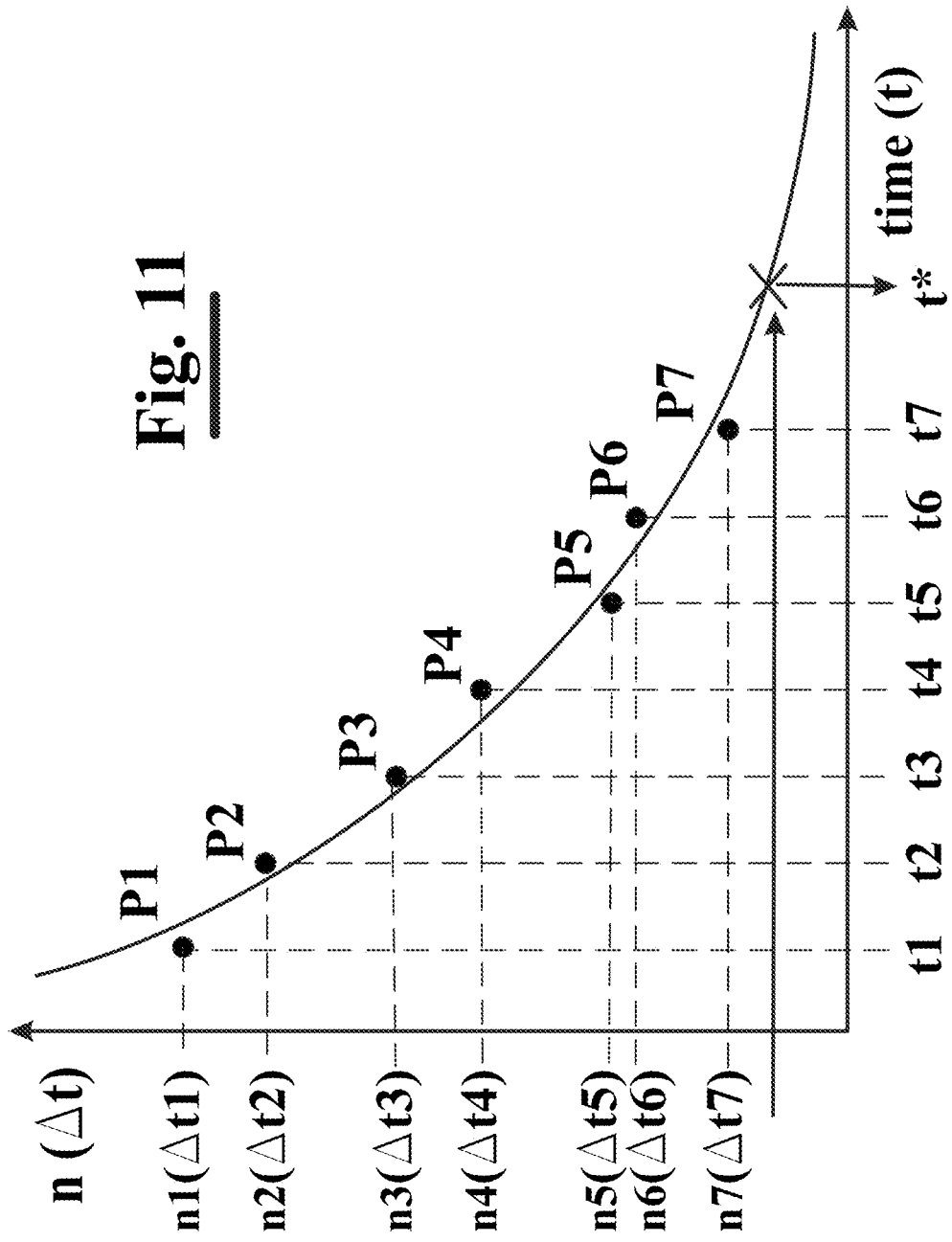
FIG. 11 shows the curve for determining the time of discharge that can be constructed through the succession of steps shown in the block diagram of FIG. 10 reproduced on a diagram: number of pulses in the time range in function of the time.

As diagrammatically shown in FIG. 11, the construction step of the characteristic chart g can provide an interpolation step of the points Pi, in such a way that it is possible to determine with large advance, i.e. once recorded the data relative to a first period of observation, such as it is the time of discharge. Since many data are available, the interpolation allows to provide a curve highly reliable. This is a further advantage of the use of a detector device of wearable type.

Figure 12:
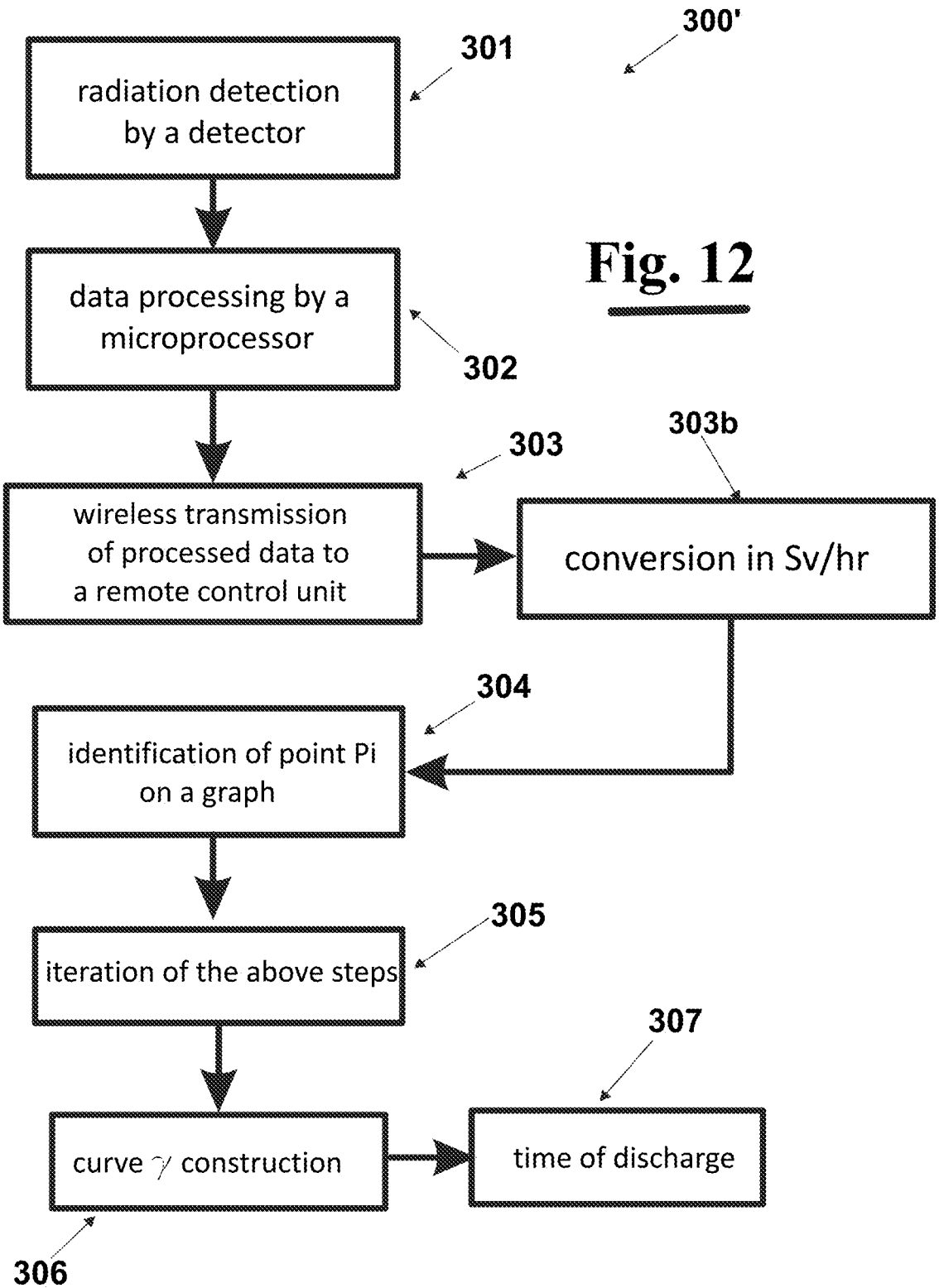
FIG. 12 shows a block diagram of a procedure similar to that one of FIG. 10 that can be carried out with the device according to the present invention but in which the number of pulses counted by the microprocessor is converted in Siever/hr.

In the exemplary embodiment shown diagrammatical view of FIG. 12 it is also provided a conversion step of each number of pulses calculated in each time range Dt1, for example 1 min, in a measure in Sievert/hr (Sv/hr), block 303b. Such a conversion can be carried out using the known curve of conversion. For example, the conversion can be necessary if the lower threshold values are expressed in Sievert/hr (Sv/hr).

Figure 13:
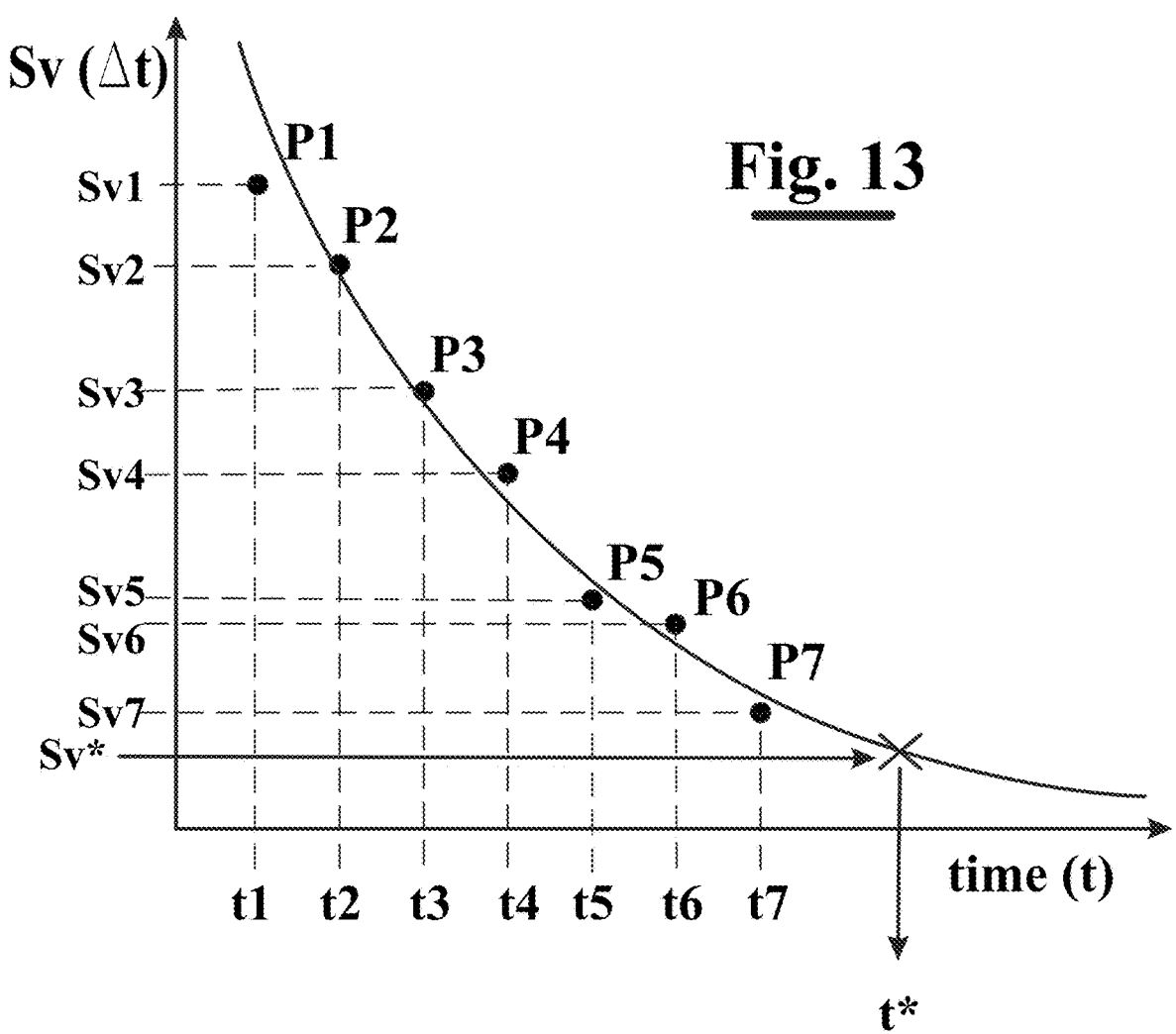
FIG. 13 shows the curve for determining the time of discharge that is obtained if a conversion of the data in Siever/hr is provided according to the succession of operations shown in FIG. 12.

In this case, therefore, the graph that is constructed is Sv/hr versus time (FIG. 13).

The foregoing description exemplary embodiments of the invention will so fully reveal the invention according to the conceptual point of view, so that others, by applying current knowledge, will be able to modify and/or adapt for various applications such embodiment without further research and without parting from the invention, and, accordingly, it is therefore to be understood that such adaptations and modifications will have to be considered as equivalent to the specific embodiments. The means and the materials to realise the different functions described herein could have a different nature without, for this reason, departing from the field of the invention. It is to be understood that the phraseology or terminology that is employed herein is for the purpose of description and not of limitation.

The invention claimed is:

1. A multiparametric device for measuring a plurality of parameters of a patient subject to a treatment with radiopharmaceuticals, said device comprising:
   a main body constrained to the patient's body, in such a way that said device for measuring, in use, is worn by the patient;
   a plurality of measurement modules, each measurement module of said plurality equipped with a sensor configured to measure a predetermined parameter of said patient;
   a microprocessor configured to process a plurality of data measured by each of said sensors of said plurality of measurement modules, obtaining a plurality of processed data;
   a wireless transmission means arranged to send via wireless communication said data processed by said microprocessor to a remote control unit;
   a supplier arranged to supply said microprocessor and each sensor of said plurality;
   engagement means arranged to engage with respective engagement means of each measurement module of said plurality, said engagement means arranged to operatively connect said microprocessor with each sensor of said plurality;
   wherein at least one measurement module of said plurality is a measurement module of radiations equipped with a radiation sensor configured to measure said radiations in a predetermined time range (Dt);
   wherein said measurement module is configured to be arranged at a distance from the patient's body in such a way that said radiation sensor is arranged to measure the radiations emitted by the source of radiations from a fixed distance; and
   wherein said control unit is arranged to carry out a processing procedure of said processed data for determining the time of discharge (td) of said patient subject to said treatment with radiopharmaceuticals;
   wherein said processing procedure comprises the steps of:
   constructing a characteristic curve (g) representative of the number of radiations detected by said sensors of radiations in function of the time;
   determining a time (t) at which said characteristic curve (g) assumes a value equal to, or lower than, a predetermined lower threshold value (t*), said time (t) corresponding to the time of discharge of the patient;
   wherein said constructing step of said characteristic curve (g) provides the steps of:
   counting the number of pulses emitted by said radiation sensor when said radiations are detected in a predetermined time range ($\Delta t1$) obtaining the number of pulses in said time range (n($\Delta t1$));
   identifying a point representative of said number of pulses (n($\Delta t1$)) on a graph (n($\Delta t1$)) versus time (t);
   repeating said counting step and said identifying step for a predetermined number (k) of time range (Dt1) with a delay one from the subsequent one of a second predetermined time range ($Dt_2$) for an overall time of detection ($Dt_{tot}$), at the end of said repeating step being determined the number (k) of radioactive particles in a predetermined time range (ni($Dt_1$)), with i=1 ... k and identified a corresponding number (k) of points (Pi) on said graph;
   constructing said characteristic curve (g) on said graph through said plurality of points (Pi), each point (Pi) of said plurality corresponding to a number of pulses ($n_i(Dt_1)$) counted at a i-th second time range ($Dti_2$);
   determining said time of discharge (td) of the patient from said characteristic curve (g), through the steps of:
   comparing said constructed characteristic curve (g) with a plurality of predetermined calibration curves;
   selecting among said plurality of calibration curves a selected calibration curve (g*) which better approximates said constructed characteristic curve (g);
   identifying on said selected calibration curve (g*) the time (t) at which said selected calibration curve (g*) assumes a value equal to, or lower than, said predetermined lower threshold value (n*($Dt_1$)).

2. The device, according to claim 1, wherein said engagement means of each of said measurement module and said engagement means of said main body are arranged to provide a positive engagement, said engagement means being configured to recognize said module, to avoid that a module can be connected to said main body at a wrong connection port.

3. The device, according to claim 1, wherein, in addition to said measurement module for measuring the radiations emitted by the patient's body, at least one measurement module is further provided selected from the group consisting of:
   a measurement module configured to measure the arterial pressure;
   a measurement module configured to measure the cardiac frequency;
   a measurement module configured to measure SpO2;
   a measurement module configured to measure the position;
   a measurement module configured to measure the temperature;
   a measurement module configured to measure ECG V4 derivations;
   a measurement module configured to measure the frequency breath;
   or a combination thereof.

4. The device, according to claim 1, wherein said remote control unit is arranged to carry out a digital filtering of said plurality of data transmitted via wireless communication from said microprocessor, said digital filtering arranged to reduce noises which are possible distortions owing to the wireless transmission of the signal associated with said plurality of data.

5. The device, according to claim 1, wherein said measurement module of the radiations is provided with a shielding element arranged to insulate said sensor of radiations from said wireless transmission means, in order to avoid interferences between the wireless transmission and the detection of radiations carried out by the radiation sensor.

6. The device, according to claim 4, wherein said shielding element is a thin plate of predetermined thickness made of a metal material.

7. The device, according to claim 5, wherein said metal material is aluminium.

8. The device, according to claim 1, wherein said radiation sensor is a solid state sensor, in such a way to allow to reduce its size and to ensure at the same time precise measurements of the energy associated with the radiations emitted by the patient's body.

9. The device, according to claim 1, comprising:
   a first measurement module of the radiations, said first module equipped with a first radiation sensor configured to measure a first plurality of radiation data at a first zone of analysis of the patient's body;

at least a second measurement module of the radiations, said second measurement module equipped with a second radiation sensor configured to measure a second plurality of radiation data at a second zone of analysis of the patient's body.

10. The device, according to claim 1, wherein said radiation sensor is arranged to emit an impulse, or "spike", at each detection of radiations emitted by the patient and said microprocessor is arranged to count the number of pulses emitted by said radiation sensor in a predetermined time range ($Dt_1$) obtaining the number of pulses in said time range ($n(Dt_1)$).

11. The device, according to claim 1, further comprising a display connected to each of said sensors, wherein said display is arranged to display said main parameters measured by each of said sensors.

12. The device, according to claim 1, wherein said plurality of measurement modules are measurement modules of radiations of different types, wherein each of said measurement modules of radiations of different types has a radiation sensor that is sensitive to a predetermined range of radiations that is different from that of other radiation sensors.

* * * * *